United States Patent
Koenig et al.

(10) Patent No.: US 10,667,849 B2
(45) Date of Patent: Jun. 2, 2020

(54) MINIMALLY INVASIVE SURGERY (MIS) ASSEMBLY

(71) Applicant: Premia Spine Ltd., Ramat Poleg (IL)

(72) Inventors: Winfried Koenig, Tuttlingen (DE); Franz Jakoubek, Liptingen (DE); Ofer Vikinsky, Zur-Igal (IL)

(73) Assignee: Premia Spine Ltd., Ramat Poleg (IL)

( * ) Notice: Subject to any disclaimer, the term of this patent is extended or adjusted under 35 U.S.C. 154(b) by 600 days.

(21) Appl. No.: 15/315,424

(22) PCT Filed: Jun. 3, 2015

(86) PCT No.: PCT/IB2015/054207
§ 371 (c)(1),
(2) Date: Dec. 1, 2016

(87) PCT Pub. No.: WO2015/186080
PCT Pub. Date: Dec. 10, 2015

(65) Prior Publication Data
US 2017/0196601 A1    Jul. 13, 2017

Related U.S. Application Data

(60) Provisional application No. 62/089,893, filed on Dec. 10, 2014, provisional application No. 62/006,914, filed on Jun. 3, 2014.

(51) Int. Cl.
*A61B 17/56* (2006.01)
*A61B 17/58* (2006.01)
(Continued)

(52) U.S. Cl.
CPC .... *A61B 17/7091* (2013.01); *A61B 17/00234* (2013.01); *A61B 17/708* (2013.01);
(Continued)

(58) Field of Classification Search
CPC ............. A61B 17/7091; A61B 17/708; A61B 17/7086; A61B 17/7092; A61B 17/888;
(Continued)

(56) References Cited

U.S. PATENT DOCUMENTS

2004/0215190 A1* 10/2004 Nguyen ............. A61B 17/1671
606/86 A
2009/0228013 A1* 9/2009 Bourque ............ A61B 17/1617
606/80

(Continued)

FOREIGN PATENT DOCUMENTS

| CN | 102596288 | 7/2012 |
|---|---|---|
| DE | 102006030407 | 1/2008 |
| WO | 2012/125578 | 9/2012 |

OTHER PUBLICATIONS

PCT Search and Written Opinion PCT/IB2015/054207, dated Nov. 30, 2015.
(Continued)

*Primary Examiner* — Jessica Weiss
(74) *Attorney, Agent, or Firm* — Dekel Patent Ltd.; David Klein

(57) ABSTRACT

A surgical tool adaptor (10) includes a distal interface member (12) and a proximal holder (14). The surgical tool adaptor is formed with a lumen (16) through the distal interface member and the proximal holder for passing a guiding element (24), e.g. a K-wire, distally through the distal interface member. The proximal holder includes a locking element (26) for locking the guiding element in the lumen and the distal interface member includes a connecting element (18) for connecting to a surgical tool. The proximal holder is movable relative to the distal interface member so that the proximal holder is movable to a position wherein the guiding element does not protrude proximally out of the proximal holder.

10 Claims, 9 Drawing Sheets

(51) Int. Cl.
*A61B 17/88* (2006.01)
*A61B 17/70* (2006.01)
*A61B 17/00* (2006.01)
*A61B 90/00* (2016.01)

(52) U.S. Cl.
CPC ...... *A61B 17/7086* (2013.01); *A61B 17/7092* (2013.01); *A61B 17/888* (2013.01); *A61B 17/8897* (2013.01); *A61B 2017/00292* (2013.01); *A61B 2090/064* (2016.02); *A61B 2090/065* (2016.02)

(58) Field of Classification Search
CPC ............ A61B 17/8897; A61B 17/8875; A61B 17/8877; A61B 17/8883; A61B 17/8886; A61B 17/8888; A61B 17/8891; A61B 17/8894; A61B 2090/064–065; A61B 2017/00292; A61B 2017/90
USPC ........... 606/103–104, 86 A, 96–98, 86 R, 80
See application file for complete search history.

(56) References Cited

U.S. PATENT DOCUMENTS

| | | |
|---|---|---|
| 2010/0331897 A1 | 12/2010 | Lindner |
| 2012/0179119 A1 | 7/2012 | Ng et al. |
| 2013/0338669 A1 | 12/2013 | Brianza |
| 2014/0025117 A1* | 1/2014 | Assell ................ A61B 17/7074 606/258 |
| 2014/0094822 A1 | 4/2014 | Baynham et al. |

OTHER PUBLICATIONS

Berg Y et al, "Q-switching an all-fiber laser using acousto-optic null coupler", Applied Physics B: Lasers and Optics, Springer Berlin, Germany, vol. 111, No. 3, May 2013, pp. 425-428.

* cited by examiner

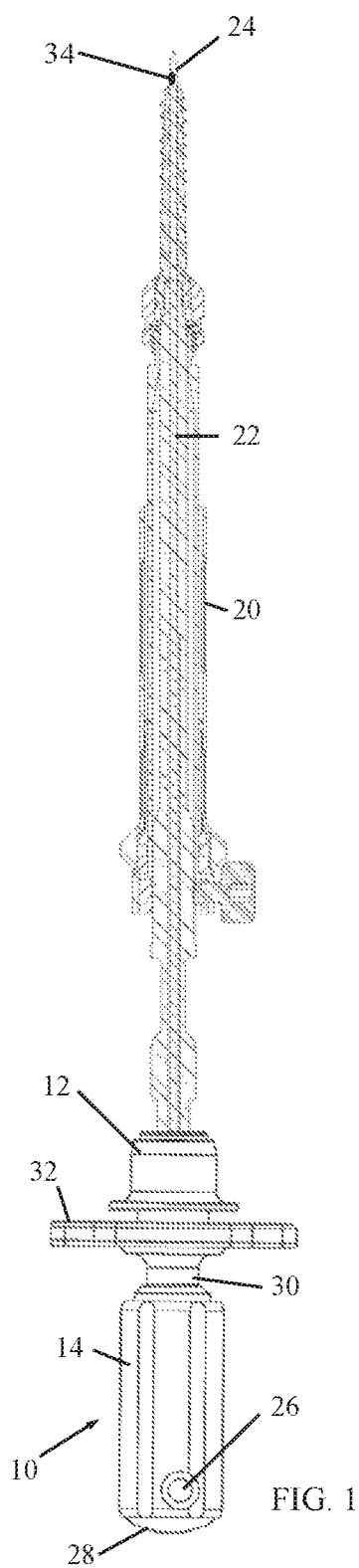
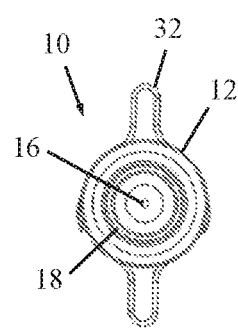
FIG. 2
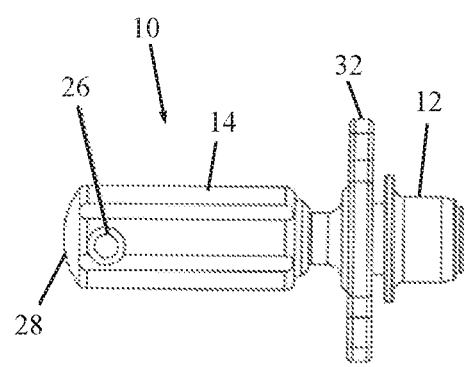
FIG. 3
FIG. 1

MINIMALLY INVASIVE SURGERY (MIS) ASSEMBLY

FIELD OF THE INVENTION

The present invention relates generally to methods and apparatus for minimally invasive surgery on spinal structures, such as for the fixation of vertebrae relative to each other, wherein pedicle screws are affixed to vertebral pedicles and rods are used to rigidly join the pedicle screws of plural vertebrae.

BACKGROUND OF THE INVENTION

Prior surgical techniques for affixing rods to vertebrae entailed relatively long incisions to provide access to the vertebrae. Current techniques use minimally invasive surgery (MIS), in which multiple percutaneous incisions are made at chosen locations rather than a single long incision. The MIS techniques are preferable because they reduce blood loss, reduce patient morbidity and shorten recovery time and hospital stay.

Minimally invasive pedicle screw fusion involves the following basic steps. First, screws are placed percutaneously through the pedicle into the vertebral body, such as over a guide wire or K-wire, guided by imaging such as fluoroscopy. One screw may be used or two (right and left sides). Second, the screws are connected with a rod. In fusion, the rod and screws are locked together. In dynamic stabilization, the rod or rod-like device (flexible connector) is bendable, but the process of inserting the bendable rod is the same as that for fusion. For example, the rod or other flexible connector fits within the screw heads, but may also include an element (a shock absorber, a spring, etc.) that allows some motion. The variations between different minimally invasive systems mostly arise in the method of placing the rod and locking the rod with the screws through a minimal incision.

The insertion of the rod through the screw heads and locking of the rod with the screws are the steps that are currently most difficult through a minimal incision. The guidance element mentioned above, such as a guide wire or K-wire, is placed percutaneously through the pedicle. Percutaneous cannulated drills and screw taps are inserted over the guidance element/wire to prepare the tract through the pedicle and vertebral body for pedicle screw insertion. Dilating tubes and a guidance tube or a retractor system are often used to dilate and hold open the path around the guidance element through skin and muscle to reduce injury to muscle and tissue when pedicle screws and insertion tools are inserted. Pedicle screws are inserted over the guidance elements either with or without passage through a guidance tube/retractor. In order to place the rod and locking assembly into the screw heads, each screw head is associated with a tower that extends through the skin incision. The tower has to accommodate the rod and locking assemblies so it is typically larger than the maximum diameter of the screw head.

Once the towers are in place, the rod is then inserted through one of a variety of methods. In one method, two or three towers (for one or two-level fusion, respectively) are coupled together to align the towers, and the rod is swung around through a separate incision superior or inferior to the towers in a pendulum fashion. Once the rod is swung in place, locking caps are placed through the towers and tightened. In another method, the rod is inserted through one of the towers and then turned approximately 90° to capture the other screws in the other towers. Inserting the rod through the screw heads in a minimally invasive system is sometimes tedious and frustrating.

As mentioned before, a K-wire or similar guide wire or guide element (the terms being used interchangeably throughout) is used in combination with a cannulated surgical tool, such as a screwdriver, tap, bore, awl, probe, or jamshidi needle, to name some. The K-wire is inserted through the lumen (cannula) of the surgical tool and penetrates into the bone, which if not done properly can injure the patient, particularly if the K-wire encounters certain sensitive tissues. The procedures often require the use of force which can cause an otherwise properly positioned K-wire to move forward into the surgical site, which if excessive can move into contact where contact is to be avoided.

In the example of screwing a pedicle screw with a pedicle screwdriver, if the K-wire is not properly positioned or inserted, the screw can slip at the point of entry and cause the surgeon to screw the pedicle screw at the wrong orientation.

SUMMARY OF THE INVENTION

The present invention seeks to provide improved devices and methods for affixing pedicle screws to vertebral pedicles and mounting rods to the pedicle screws, such as for fusion or dynamic stabilization, as described more in detail hereinbelow.

In one embodiment, the device enables inserting a K-wire through a lumen of a cannulated surgical tool. In the case of a screwdriver, for example, the K-wire also passes through the lumen of the screw. The device is easily used to position the K-wire so it protrudes a little bit (e.g., a few mm) beyond the distal tip of the screw or surgical tool. The device is then used to capture the K-wire with respect to the screw or tool. The device is adjustable so that its proximal end is flush with the proximal end of the K-wire, so that the surgeon can hammer or otherwise apply force on the proximal end of the device in order to advance the K-wire and screw or tool together. The K-wire breaches the cortical bone (or other spinal structure which the surgeon wishes to breach) and brings the tip of the cannulated screw or tool to the bone surface. From there, the surgeon can screw in the pedicle screw or advance the tool without concern for slipping. Without the device, the screw or tool can slip at the point of entry. The invention saves time and effort to insert screw or other surgical tools.

In the prior art, such as with using a jamshidi needle, the surgeon cannot readily feel if the cutting tool has cut through to sensitive tissue. The surgeon must work under X-ray or other imaging because the surgeon does not feel the jamshidi needle or other tool breaching the cortical bone. In contrast, in the present invention, the K-wire is pedicle guided, which means the K-wire can be moved back (proximally) with smaller risk of breaching. The controlled protuberance of the K-wire from the end of the pedicle and other features of the invention also help, such as a force sensor described below.

There is thus provided in accordance with an embodiment of the present invention a surgical tool adaptor including a distal interface member and a proximal holder, the surgical tool adaptor being formed with a lumen through the distal interface member and the proximal holder for passing a K-wire distally through the distal interface member, the proximal holder including a capturing element for capturing the K-wire in the lumen and the distal interface member including a connecting element for connecting to a surgical tool, wherein the proximal holder is movable relative to the distal interface member so that the proximal holder is movable to a position wherein the K-wire does not protrude proximally out of the proximal holder.

The proximal holder may be threadingly mounted on a shaft and rotation of the proximal holder on the shaft may move the proximal holder axially relative to the distal interface member.

In accordance with an embodiment of the present invention the proximal holder includes a proximal face for striking with a striking tool.

The connecting element may include a threaded element or a male or female connector for connection with the surgical tool. A handle may be positioned near the distal interface member for turning the surgical tool adaptor. The proximal holder may be rotatable with respect to the distal interface member.

There is also provided in accordance with an embodiment of the present invention an assembly including a surgical tool adaptor including a distal interface member and a proximal holder, the surgical tool adaptor being formed with a lumen through the distal interface member and the proximal holder, a surgical tool with a lumen, and a K-wire that passes distally through the distal interface member and the surgical tool, the proximal holder including a capturing element for capturing the K-wire in the lumen of the surgical tool adaptor and the distal interface member including a connecting element for connecting to the surgical tool, wherein the proximal holder is movable relative to the distal interface member so that the proximal holder is movable to a position wherein the K-wire does not protrude proximally out of the proximal holder and wherein the K-wire passes a predetermined amount beyond a distal tip of the surgical tool.

The surgical tool may include a screw, a screwdriver, a tap, a bore, an awl, a probe, or a jamshidi needle, and others.

There is also provided in accordance with an embodiment of the present invention a method including passing a K-wire distally through the distal interface member of the surgical tool adaptor so that the K-wire does not protrude proximally out of the proximal holder and the K-wire passes a predetermined amount beyond the distal tip of the surgical tool, and striking a proximal face of the proximal holder to drive the K-wire into a bone surface, thereby bringing the distal tip of the surgical tool to the bone surface, and further advancing the surgical tool to penetrate in the bone surface.

BRIEF DESCRIPTION OF THE DRAWINGS

The present invention will be understood and appreciated more fully from the following detailed description taken in conjunction with the drawings in which:

FIG. 1 is a simplified side-view, partially sectional illustration of a surgical tool adaptor connected to a surgical tool, constructed and operative in accordance with an embodiment of the present invention;

FIG. 2 is a simplified end-view illustration of the surgical tool adaptor;

FIG. 3 is a simplified side-view illustration of the surgical tool adaptor;

DETAILED DESCRIPTION OF EMBODIMENTS

Figure 4:
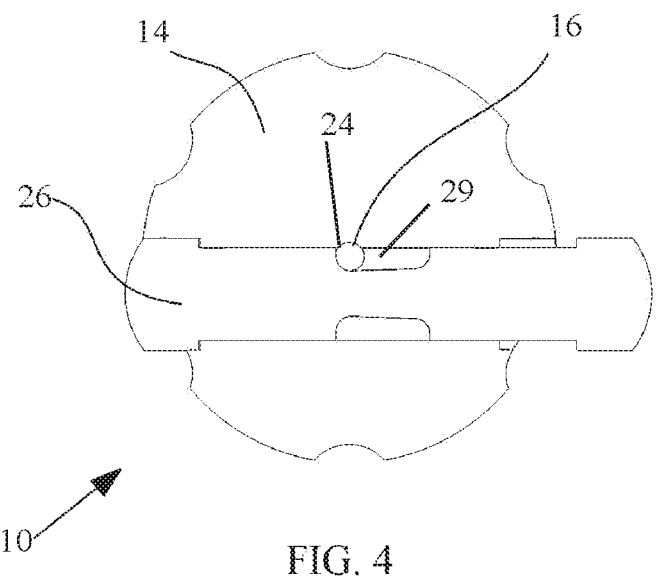
FIG. 4 is a simplified illustration of capturing the K-wire in the adaptor.
Figure 5:
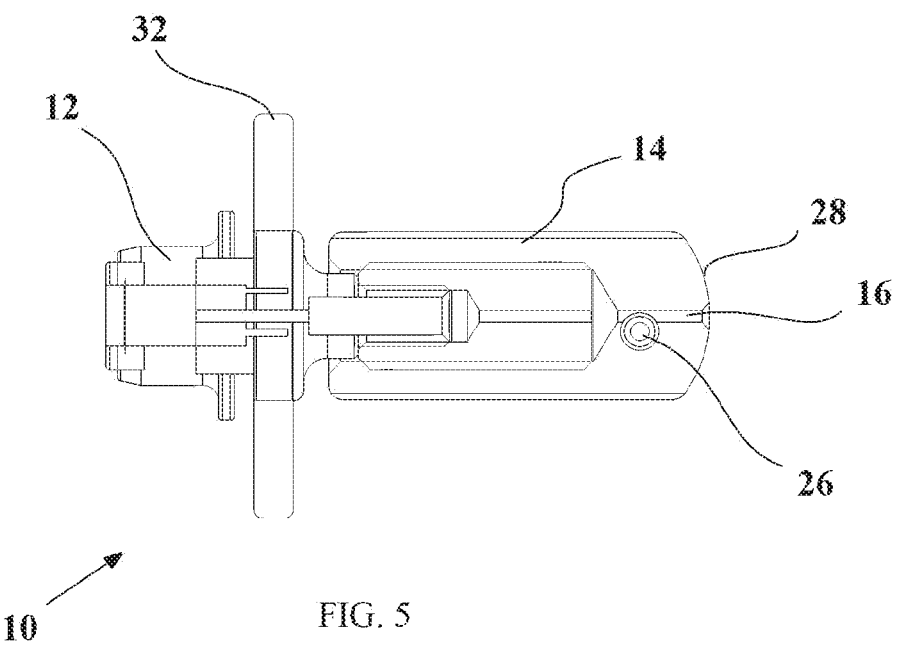
FIG. 5 is another side-view illustration of the adaptor.

Reference is now made to FIGS. 1-5, which illustrate a surgical tool adaptor 10, constructed and operative in accordance with a non-limiting embodiment of the present invention.

The surgical tool adaptor 10 includes a distal interface member 12 and a proximal holder 14. Surgical tool adaptor 10 is formed with a lumen 16 (the central bore in FIG. 2 and FIG. 5) through distal interface member 12 and proximal holder 14. Distal interface member 12 includes a connecting element 18 (FIG. 2) for connecting to a surgical tool 20 (FIG. 1). The connecting element 18 may include, without limitation, a threaded element (such as an internally threaded bore) or a male or female connector for connection with the surgical tool 20.

The surgical tool 20 may include, without limitation, a screw, a screwdriver (the tool shown in the illustrations), a tap, a bore, an awl, a probe, or a jamshidi needle and others. Surgical tool 20 is formed with a lumen 22 (FIG. 1). Two or more surgical tools may be connected to each other, such as a screwdriver connected to a pedicle screw, as seen in FIG. 1.

A K-wire 24 passes through lumen 16 of surgical tool adaptor 10 distally through distal interface member 12 into lumen 22 of surgical tool 20 and distally out the distal tip of surgical tool 20 (the distal end of K-wire 24 is seen in FIG. 1). Proximal holder 14 includes a capturing element 26 (such as, but not limited to, a set screw) for capturing K-wire 24 in lumen 16 of surgical tool adaptor 10. As seen in FIG. 4, capturing element 26 may be a pin with a recess 29 against which K-wire 24 can be captured.

Proximal holder 14 is movable relative to distal interface member 12 so that proximal holder 12 is movable to a position wherein K-wire 24 does not protrude proximally out of proximal holder 14; that is, K-wire 24 is either flush with, or inwards of, the proximal face 28 of proximal holder 14. Proximal holder 14 may be threadingly mounted on a shaft 30 and rotation of proximal holder 14 on shaft 30 moves proximal holder 14 axially relative to distal interface member 12. The proximal face 28 is adapted for striking with a striking tool, such as a hammer or other tool (not shown).

A handle 32 may be fixed to shaft 30 and positioned near distal interface member 12 for turning surgical tool adaptor 10. Proximal holder 14 may be rotatable with respect to distal interface member 12 by being mounted on bearings.

In use, the surgeon passes K-wire 24 distally through distal interface member 12 of surgical tool adaptor 10 so that K-wire 24 does not protrude proximally out of proximal holder 14. The surgeon moves or adjusts K-wire 24 so it passes a predetermined amount (e.g., a few mm) beyond the distal tip of surgical tool 20. The surgeon positions the assembly on a bone surface and strikes proximal face 28 of proximal holder 14 to drive K-wire 24 into the bone surface, thereby bringing the distal tip of surgical tool 20 to the bone surface. The surgeon then advances surgical tool 20 to penetrate in the bone surface.

In another embodiment of the invention, proximal holder 14 may be adjustable to accommodate different lengths of K-wires and different surgical tools. In this manner, for example, after adjusting the amount the K-wire protrudes from the distal end of a first surgical tool, the first surgical tool can be removed and a second surgical tool may be used, and the surgeon can adjust the position of the adaptor with respect to the K-wire so as to achieve the desired amount the K-wire protrudes from the distal end of the second surgical tool while at the same time making the proximal end of the K-wire flush with the proximal face 28 of proximal holder 14. For example, proximal holder 14 may be made of two parts that can be spaced axially from one another (such as by threaded connection).

In another embodiment of the invention, a pedicle screw is provided with a built-in K-wire. The K-wire passes through a central lumen in the screw and protrudes out of the distal tip of the screw. Optionally, the amount of protrusion can be adjusted similarly as described above for surgical tool adaptor 10. Such a pedicle screw can serve as a self-tapping screw.

In another embodiment of the invention, a force sensor 34, such as but not limited to, a load cell or strain gauge, is mounted on the guide element (K-wire) 24 (FIG. 1). The force sensor 34 can sense and alert changes in load applied on the tip of wire 24. For example, when the wire 24 touches a cortical bone, bending of axial forces are sensed by force sensor 34, which sends a signal to a processor (not shown) that alerts the surgeon that the screw is about to breach the pedicle or vertebral body. Alternatively, the system can detect and alert when the load is reduced, for example, if the tip has crossed the pedicle into the cancellous bone.

The surgical tool adaptor 10 can adjust the length of wire 24 to adjust the sensitivity of the system. A long wire is more sensitive and alerts of danger sooner. A short wire is less sensitive.

Figure 6:
FIG. 6 is a simplified illustration of a guidance element in a flexible tube and equipped with a force sensor, in accordance with an embodiment of the present invention.

In another non-limiting example shown in FIG. 6, wire 24 passes into a hollow lumen of a flexible tube 36. The distal end of wire 24 is fixed (e.g., welded) to the distal end of tube 36. The proximal end of wire 24 is free to move and is not fixed to tube 36. The force sensor 34 is attached to the free-moving end of wire 24. When tube 36 bends, due to interaction with cortical bone, the distance between the ends of wire 24 and tube 36 shortens at the free-moving end. This shortening is detected by force sensor 34. The system can also detect axial pressure resulted from reaching the vertebral body wall.

Figures 7, 8:
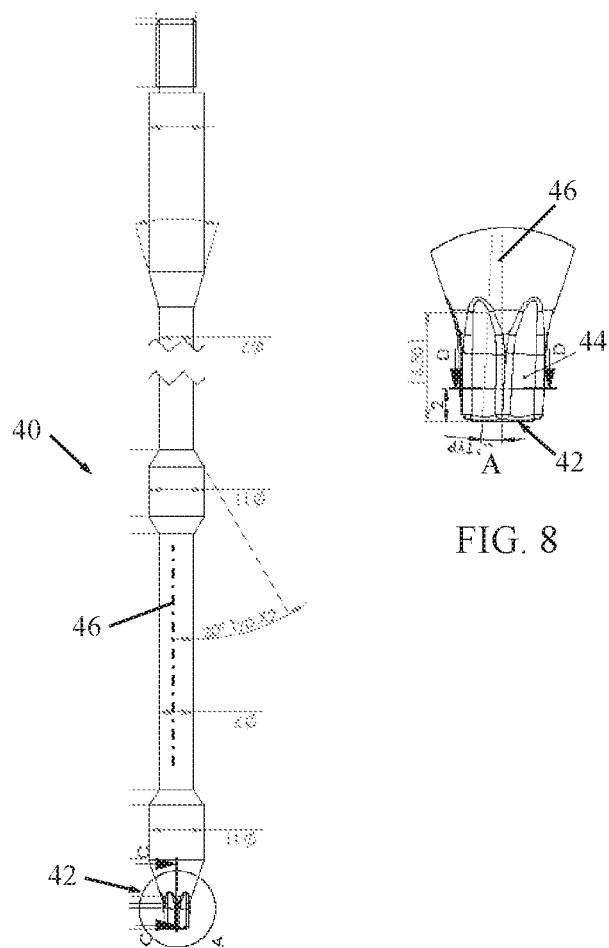
FIG. 7 is a simplified illustration of a screwdriver with a polylobular tip, constructed and operative in accordance with an embodiment of the present invention.
FIG. 8 is a simplified enlarged illustration of the screwdriver tip with swivel slots.

Reference is now made to FIG. 7, which illustrates a screwdriver 40 with a polylobular tip 42, constructed and operative in accordance with an embodiment of the present invention. In the illustrated embodiment, the tip 42 is a modified star (hexalobular) design with the lobes separated by swivel slots or grooves 44. As seen in FIG. 8, "swivel" slots means the slot are not straight and parallel to the longitudinal axis 46 of the screwdriver shaft; instead the slots are tilted or curve away from the longitudinal axis 46 by an angle A, such as but not limited to, 3°. Due to this tilt or curve, the slots lobes and slots wedge into the corresponding socket of the screw or set screw. Thus, the swivel slots 44 enable the screwdriver 40 to grip a screw or set screw and hold it in place for installation in a pedicle screw system (as seen later in FIG. 11B). The illustrated embodiment has 6 lobes but the invention is not limited to this number.

Figure 9:
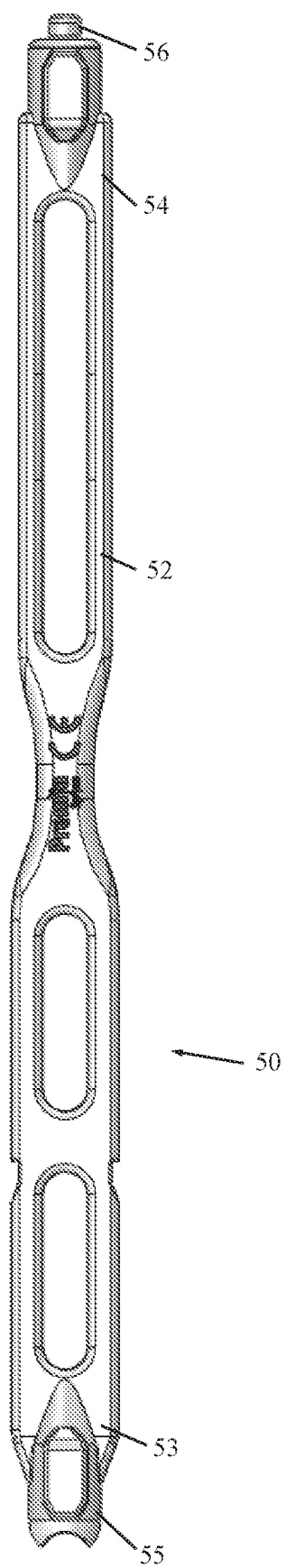
FIG. 9 is a simplified illustration of a tower guide, constructed and operative in accordance with an embodiment of the present invention.

Reference is now made to FIG. 9, which illustrates a tower guide 50, constructed and operative in accordance with an embodiment of the present invention. In the illustrated embodiment, tower guide 50 has a shaft 52 with a first end 53 and a second end 54. First end 53 has a screw head adaptor 55, e.g., configured to be placed in a tulip-head of a pedicle screw (not shown). Second end 54 has a socket adaptor 56, e.g., configured to be placed in a set screw socket (not shown).

Tower guide 50 is used to guide a tower (not shown) percutaneously onto the screw tulip after the screw has been installed. For example, the screw head adaptor 55 is placed in the tulip and aligns the screw head with tower guide 50. After tower guide 50 is properly aligned, the tower is slid over guide 50 and attached to the tulip. As another example, the socket adaptor 56 is placed in the set screw socket (e.g., TORX or Allen) and used to align the screw head with the tower guide. After tower guide 50 is properly aligned, the tower is slid over guide 50 and attached to the tulip.

Tower guide 50 is also used to release the tower from the screw tulip after final positioning and tightening of the set screws. The shaft 52 is sized to spread apart the flexible arms of the tower to release the tower from the screw tulip.

After the towers are in place, a rod can be inserted in the pedicle screw heads. For example, the towers are aligned by the surgeon and the rod ends are positioned in the rod channels of the towers (not shown). Afterwards, the rod is advanced into the polyaxial screw seat (the rod position may be verified using fluoroscopy or other imaging). If reduction of the rods is necessary the invention provides a reduction tool, as is now described.

Figure 10:
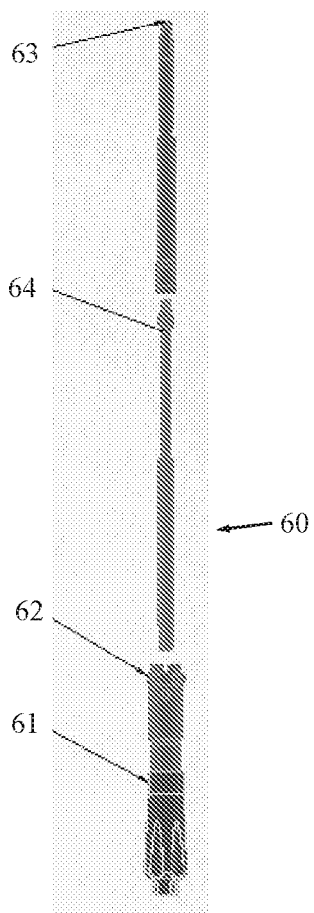
FIGS. 10, 11A and 11B are simplified illustrations of a reduction tool, constructed and operative in accordance with an embodiment of the present invention.
Figure 11B:
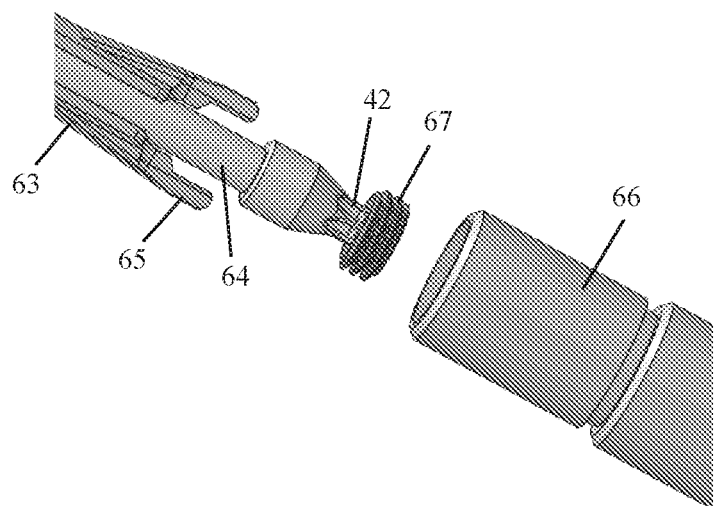
Figure 11A:
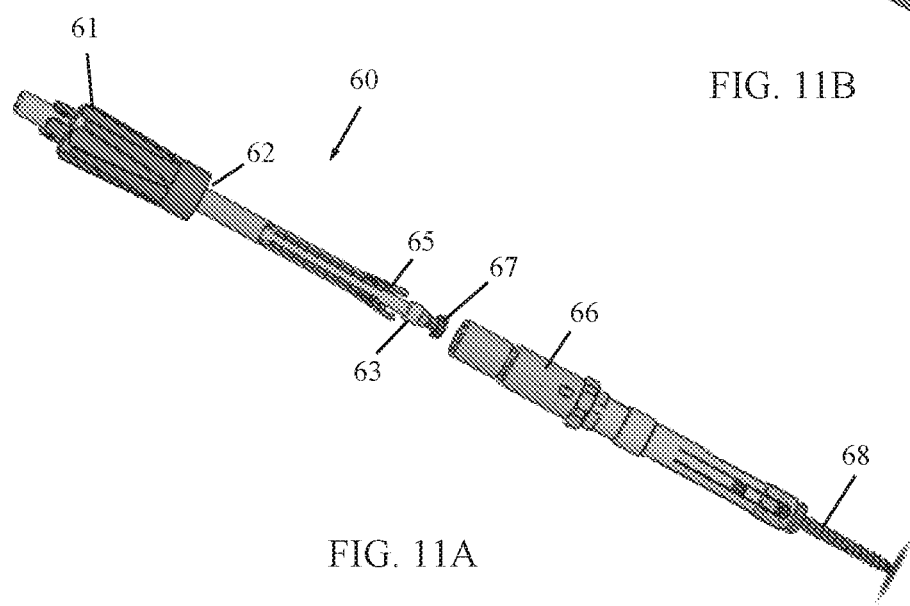

Reference is now made to FIGS. 10, 11A and 11B, which illustrate a reduction tool 60, constructed and operative in accordance with an embodiment of the present invention.

In the illustrated embodiment shown in FIG. 10, reduction tool 60 includes a reduction tool knob or handle 61, which is proximal to a tower connector 62. The distal end of tool 60 includes a reduction tool reducer 63, through which passes a screw inserter 64. As seen in FIGS. 11A and 11B, reduction tool reducer 63 has spring arms 65 which are positively received ("click") into corresponding grooves or slots (not shown) in a tower 66. Screw inserter 64 has the polylobular tip 42 which grips a set screw 67 and holds it in place for installation in a pedicle screw 68.

The reduction tool 60 is used to push a fusion rod (not shown) into the tulip saddle in case the rod seats above the tulip and the set screw 67 cannot be fastened. The reduction tool 60 is attached to tower 66. A thread mechanism in handle 61 and connector 62 is used to apply force on the rod to push it to its final position in the screw saddle.

Reference is now made to FIGS. 12A-12E, which illustrate a depth measurement gauge 70 for use with a pedicle probe 72, constructed and operative in accordance with an embodiment of the present invention. In the illustrated embodiment, depth measurement gauge 70 has a hollow lumen for the pedicle probe 72 to pass through.

Figures 12A, 12B, 12C, 12D, 12E:
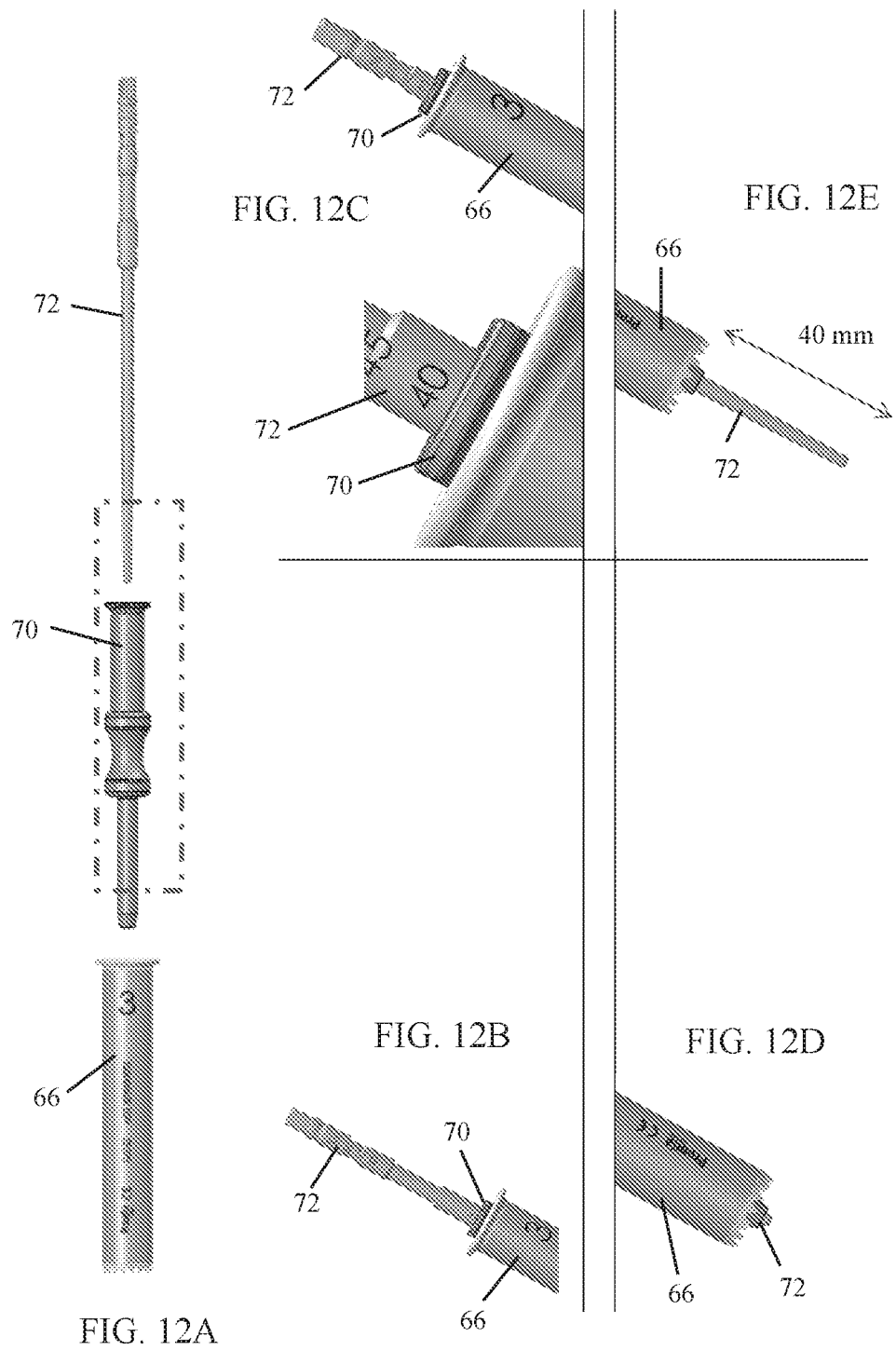
FIGS. 12A-12E are simplified illustrations of a depth measurement gauge for use with a pedicle probe, constructed and operative in accordance with an embodiment of the present invention.

In FIG. 12B, the proximal end of pedicle probe 72 is shown inside depth measurement gauge 70. The scale indicates 0, which means that the tip of probe 72 is at the pedicle entry point level.

In FIG. 12C, the proximal end of pedicle probe 72 is shown inside depth measurement gauge 70. The scale indicates a 40 mm screw length.

In FIG. 12D, the distal end of pedicle probe 72 extends out of the tower 66. The distal tip of probe 72 is at the pedicle entry point level.

In FIG. 12E, the distal end of pedicle probe 72 extends out of the tower 66. The distal tip of probe 72 extends 40 mm into the vertebral body, which indicates that the screw which should be used is 40 mm long.

Figure 13B:
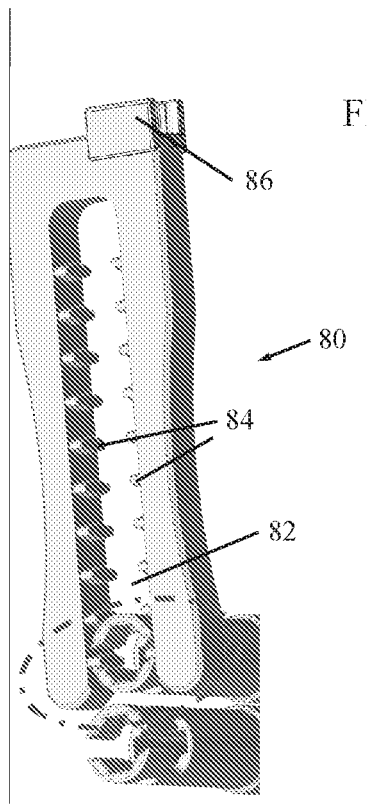
FIGS. 13A and 13B are simplified illustrations of a tower alignment tool, constructed and operative in accordance with an embodiment of the present invention.
Figure 13A:
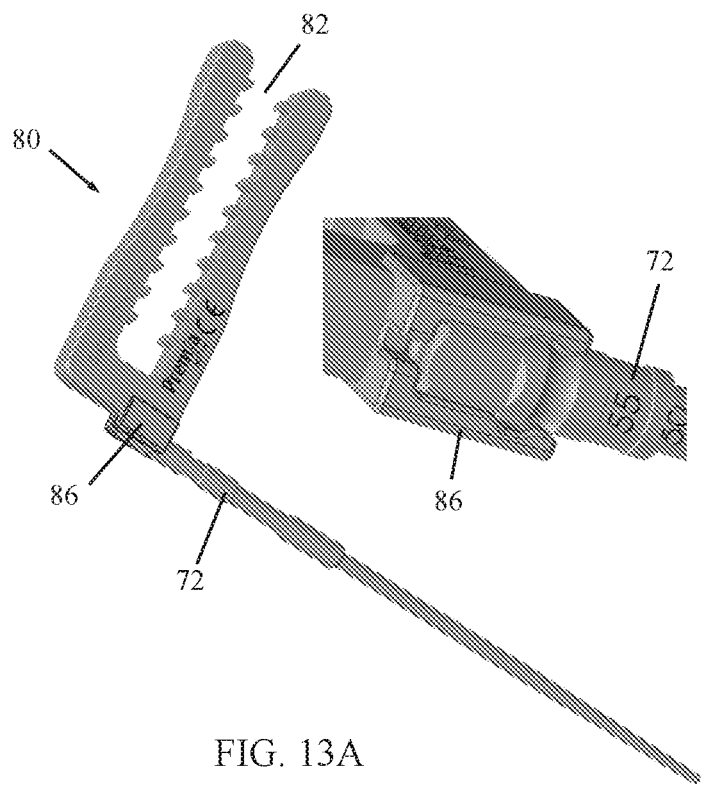

Reference is now made to FIGS. 13A and 13B, which illustrate a tower alignment tool 80, constructed and operative in accordance with an embodiment of the present invention. In the illustrated embodiment, tower alignment tool 80 has an open-ended (U-shaped) throat 82, which has a plurality of tower grabbing elements 84. The tower alignment tool 80 includes a pedicle probe attachment member 86. The U-shaped throat 82 allows attachment to a single tower in the event that two adjacent towers are too close to each other.

In FIG. 13A, tower alignment tool 80 is attached to pedicle probe 72. The alignment tool 80 is used as a handle to rotate and pull the pedicle probe 72 from the pedicle after screw placement.

What is claimed is:

1. An assembly comprising:
    a surgical tool adaptor comprising a distal interface member for connecting to a surgical tool and a proximal holder rotatable with respect to said distal interface member,
    said surgical tool adaptor being formed with a lumen through said distal interface member and said proximal holder for passing a guiding element distally through said distal interface member,
    said proximal holder comprising a proximal face configured to be struck with a striking tool and a capturing element for capturing the guiding element in said lumen, and
    said distal interface member comprising a connecting element for connecting to said surgical tool,
    wherein said proximal holder is axially movable relative to said distal interface member so that said proximal holder is movable to a position wherein the guiding element does not protrude proximally out of said proximal holder, wherein capturing of said guiding element by said capturing element is independent of movability of said proximal holder relative to said distal interface member, and wherein after said guiding element is captured, rotation of said proximal holder relative to said distal interface member moves said guiding element more distally or more proximally relative to said distal interface member.

2. The assembly according to claim 1, wherein said proximal holder is threadingly mounted on a shaft and rotation of said proximal holder on said shaft moves said proximal holder axially relative to said distal interface member.

3. The assembly according to claim 1, wherein said connecting element comprises a threaded element for threaded connection with the surgical tool.

4. The assembly according to claim 1, wherein said connecting element comprises a male or female connector for connection with the surgical tool.

5. The assembly according to claim 1, further comprising a handle positioned near said distal interface member for turning said surgical tool adaptor.

6. The assembly according to claim 1, wherein said guiding element comprises a K-wire.

7. The assembly according to claim 1, further comprising a force sensor mounted on said guiding element.

8. An assembly comprising:
    a surgical tool adaptor comprising a distal interface member and a proximal holder rotatable with respect to said distal interface member,
    said surgical tool adaptor being formed with a lumen through said distal interface member and said proximal holder;
    a surgical tool with a lumen; and
    a guiding element that passes distally through said distal interface member and said surgical tool;
    said proximal holder comprising a proximal face configured to be struck with a striking tool and a capturing element for capturing the guiding element in said lumen of said surgical tool adaptor, and said distal interface member comprising a connecting element for connecting to said surgical tool,
    wherein said proximal holder is axially movable relative to said distal interface member so that said proximal holder is movable to a position wherein the guiding element does not protrude proximally out of said proximal holder and wherein the guiding element passes a predetermined amount beyond a distal tip of said surgical tool,
    and wherein capturing of said guiding element by said capturing element is independent of movability of said proximal holder relative to said distal interface member, and
    wherein after said guiding element is captured, rotation of said proximal holder relative to said distal interface member moves said guiding element more distally or more proximally relative to said distal interface member.

9. The assembly according to claim 8, wherein said surgical tool comprises a screw, a screwdriver, a tap, a bore, an awl, a probe, or a jamshidi needle.

10. The assembly according to claim 8, wherein said guiding element comprises a K-wire.

* * * * *